United States Patent [19]

Drake

[11] Patent Number: 4,895,819

[45] Date of Patent: Jan. 23, 1990

[54] ALKALI METAL CARBONATE SUPPORTS AND ELEMENTAL ALKALI CATALYSIS THEREOF FOR OLEFIN DIMERIZATION

[75] Inventor: Charles A. Drake, Nowata, Okla.

[73] Assignee: Phillips Petroleum Company, Bartlesville, Okla.

[21] Appl. No.: 220,639

[22] Filed: Jul. 18, 1988

[51] Int. Cl.[4] ............... B01J 27/232; B01J 23/04
[52] U.S. Cl. ................... 502/174; 423/421; 502/439; 585/516
[58] Field of Search ............ 502/174, 184, 402, 439; 423/421, 426

[56] References Cited

U.S. PATENT DOCUMENTS

| 3,207,812 | 9/1965 | Keith et al. | 502/174 |
|---|---|---|---|
| 3,291,732 | 12/1966 | Keith et al. | 502/174 |
| 3,389,190 | 6/1968 | Alderson et al. | 502/174 |
| 3,846,540 | 11/1974 | Leach | 502/439 |
| 3,853,786 | 12/1974 | Forni et al. | 252/444 |
| 3,916,017 | 10/1975 | Closson et al. | 252/443 |
| 4,051,017 | 9/1977 | Beaty, Jr. | 208/135 |
| 4,172,809 | 10/1979 | Triki | 252/455 R |
| 4,407,733 | 10/1983 | Birkenstock et al. | 502/174 |
| 4,520,126 | 5/1985 | Kawamoto et al. | 502/174 |
| 4,544,790 | 10/1985 | Drake | 585/516 |
| 4,656,154 | 4/1987 | Drake | 502/174 |

FOREIGN PATENT DOCUMENTS 1170497 11/1969 United Kingdom ............ 502/174

Primary Examiner—Paul E. Konopka
Attorney, Agent, or Firm—Lynda S. Jolly

[57] ABSTRACT

Catalyst supports, catalyst systems, methods for the preparation thereof, and dimerization process therewith are provided catalyst supports are prepared from an alkali metal carbonate, water, water soluble ketone and optionally at least one carbonaceous compound. Catalyst systems comprise at least one elemental alkali metal depositd on the catalyst support. Optionally, the catalyst system further comprises at least one promoter.

17 Claims, No Drawings

ALKALI METAL CARBONATE SUPPORTS AND ELEMENTAL ALKALI CATALYSIS THEREOF FOR OLEFIN DIMERIZATION

BACKGROUND OF THE INVENTION

This invention relates to alkali metal carbonate supported alkali metal catalysts.

It is known in the art to employ alkali metal carbonate supported alkali metal catalysts for such conversions as propylene dimerization. It is also known in the art to prepare alkali metal carbonate catalyst supports by making a thick paste in water and eventually forming a pelletized, tabletted, or granular support. The support prepared in such a manner subsequently can be washed or treated with alcohol. Alkali metal carbonate catalyst supports prepared from a water-based paste are difficult to process because the alkali metal carbonate to water ratio must be closely controlled or the paste can have the wrong consistency. Thus, it can be difficult to process and easily form a useable catalyst support.

SUMMARY OF THE INVENTION

It is an object of this invention to provide a process to easily prepare an alkali metal carbonate catalyst support.

It is a further object of this invention to provide an easily processed alkali metal carbonate catalyst support.

It is yet another object of this invention to provide a method to prepare an improved alkali metal carbonate supported elemental alkali metal catalyst system.

It is yet a further object of this invention to provide an improved catalyst system for the dimerization of olefins.

It is yet another object of this invention to provide an improved process for the dimerization of olefins.

In accordance with the present invention, an alkali metal carbonate catalyst support is prepared from a thick paste comprising an alkali metal carbonate, water, and a water soluble ketone. The resultant thick paste is formed into a particulate product and calcined to give a durable catalyst support.

DESCRIPTION OF THE PREFERRED EMBODIMENTS

The present invention provides a process to prepare a catalyst support which comprises the steps of forming a thick paste comprising an alkali metal carbonate, water, and a water soluble ketone; forming a particulate product from said paste; and calcining said particulate product. The particulate product can be formed by grinding and seiving prior to calcining, or it can be formed into an extrudate, pellets, tablets, pills, or any other granular form prior to calcining.

In accordance with one embodiment of the invention, the thick paste comprising an alkali metal carbonate, water, and a water soluble ketone can further comprise a carbonaceous compound.

In accordance with yet another embodiment of the invention, the previously prepared particulate alkali metal carbonate catalyst support can be contacted with at least one elemental alkali metal to produce a catalyst composition.

In accordance with yet a further embodiment of the invention, the alkali metal carbonate catalyst support and the elemental alkali metal catalyst composition can be contacted with at least one promoter.

Supports

Commercially available alkali metal carbonate, in the form of powder, granules, or the like, is mixed with just enough water and ketone to form a thick paste. This thick paste comprises about 15 to about 95 weight percent dried alkali metal carbonate, about 8 to about 30 weight percent water soluble ketone, and about 10 to about 23 weight percent water, all based on the total weight of the support. More preferably, the thick paste comprises about 65 to about 75 weight percent dried alkali metal carbonate, about 9 to about 19 weight percent water soluble ketone, and about 11 to about 19 weight percent water; most preferably the thick paste comprises about 67 to about 72 weight percent alkali metal carbonate, about 11 to about 18 weight percent water soluble ketone and about 15 to about 18 weight percent water for best formation of a particulate produce. Generally, if larger quantities of the alkali metal carbonate support are prepared, less water and water soluble ketone will be necessary.

The alkali metal carbonate support can optionally contain at least one carbonaceous compound. The carbonaceous compound can be added simultaneously with the alkali metal carbonate, water soluble ketone, and water. For purposes of this disclosure, the term "carbonaceous compound" is intended to include various forms of the element carbon, including, but not limited to carbon black, charcoal, coconut charcoal, amorphous graphite, crystallite graphite, and the like, as well as mixtures of any two or more thereof. Finely divided graphite is presently preferred because it is useful both as a die lubricant for the pelleting process and it imparts improved activity to the finished dimerization catalyst. The carbonaceous compound, if employed, comprises from about 0.01 to about 20 weight percent of the total alkali metal carbonate support. Preferably, the carbonaceous compound comprises about 0.1 to about 10 weight percent, and most preferably, the carbonaceous compound comprises about 0.3 to about 5 weight percent of the support.

Any alkali metal carbonate can be used in the preparation of the catalyst support. Preferably, sodium carbonate or potassium carbonate are used and most preferably, potassium carbonate is used.

Water soluble ketones suitable for use in preparation of the catalyst support are straight chain and branched aliphatic ketones having from about 3 to about 7 carbon atoms. Suitable ketones include, but are not limited to, 2-propanone (acetone), 2-butanone (methylethylketone), 3-pentanone, 2-hexanone, and mixtures thereof. Preferably, 2-propanone and/or 2-butanone are used to prepare the alkali metal carbonate catalyst support.

The thick paste can then be formed into a particulate product prior to calcining. The paste can be formed into an extrudate using an extruder. The extrudate can be any diameter, but for best catalytic activity and ease of handling and processability, the extrudate is from about 1/16 to about ¼ inch in diameter. After the extrudate passes through the die, the extrudate can be cut into uniform lengths, if desired. However, uniform lengths are not always necessary, so the extrudate can be allowed to break on its own, into any length. If the extrudate is allowed to break on its own, it will usually have a length of about 2 to about 7 times the diameter width. Usually, the extrudate is allowed to break of its own accord because of ease of manufacture.

The thick paste after drying and granulation can also be formed into tablets using a die press, a punch press, or a pelleting machine. Tablets are usually very uniform in size. Tablets look similar to an extrudate, except the two ends of each cylindrical tablet are convex, not blunt.

The thick paste can also be formed into pellets and/or pills. Pellets and pills can be defined as any other type of form that are not prepared using an extruder, a die press, punch press, or pelleting machine. One example of an apparatus used to make pellets or pills is a disk spherudizer. A disk spherudizer, or disk pelletizer, is a flat, circular disk with a lip perpendicularly attached around the circumference of the disk. The disk is mounted at an angle and rotates; scrapers are stationarily mounted above the disk. The disk rotating speed, angle of the disk, solids feed rate onto the disk, and ratio of liquids to solids all control the diameter of the pellets. Usually, the solids and liquids are not mixed prior to introduction onto the disk, but they can be pre-mixed.

Another method of forming a particulate product from the thick paste is to oven dry the thick paste under conditions of time and temperature sufficient to insure that substantially all of the water and water soluble ketone has been driven off. The dried paste can then be broken into pieces and fractionated by suitable means such as, for example, by passing through the appropriate mesh size screen seives to recover a desired particle size fraction.

After formation of the extrudate, tablets, pellets, or pills, the catalyst support should be dried under conditions of time and temperature sufficient so that substantially all of the water and water soluble ketone are driven off. Usually, a temperature in the range of about 80° to about 350° C., preferably a temperature in the range of about 85° to about 150° C., for at least 2 hours is sufficient. Drying can occur under any atmosphere, but for safety reasons, a vacuum oven is usually employed.

Once the catalyst support is formed and dried, it should be calcined in an oxygen-containing atmosphere at a temperature in the range of about 80° to about 350° C., preferably about 250° C., for a time of at least 2 hours. Upon completion of calcination, the catalyst support can be stored in a dry atmosphere. Preferably, the catalyst support is stored under a dry, oxygen-free atmosphere until needed for further treatment.

Catalysts and Promoters

Catalysts systems employed in the practice of this invention comprise one of the alkali metal carbonate supports described above, at least one elemental alkali metal catalyst, and optionally one or more of the following additional promoters:
elemental copper,
elemental cobalt,
finely divided stainless steel,
finely divided glass, and
mixtures of two or more thereof.
It should be recognized, however, that the catalyst systems of the invention can contain additional components which do not adversely affect the catalyst performance, such as, for example, pigments, dyes, processing aids, inert fillers, binders and the like.

The alkali metals contemplated to be within the scope of the invention include lithium, sodium, potassium, rubidium and cesium. While the proportion of alkali metal combined with the alkali metal carbonate support can vary appreciably, generally at least about one weight percent of alkali metal based on the total weight of treated support will be employed. Generally, about 1 to about 20 weight percent alkali metal will be employed with about 2 to about 15 weight percent preferred. An alkali metal loading of about 3 to about 10 weight percent based on the total weight of treatment support is most preferred for most efficient use of reagents, high catalyst activity and selectivity, and ease of catalyst preparation. Potassium is the preferred elemental alkali metal due to its ready availability as well as ease and safety in handling.

The proportion of optional promoter on the alkali metal carbonate support can vary appreciably, but generally, at least one weight percent of the optional promoter based on the total weight of treated support will be employed. The following amounts are provided for additional guidance:

| Promoter | Loading, Weight Percent | | |
|---|---|---|---|
| | Broad | Intermediate | Preferred |
| Cu | 1–30 | 3–20 | 5–12 |
| Co | 1–50 | 3–25 | 5–15 |
| *SS | 1–80 | 3–60 | 5–50 |
| Glass | 1–50 | 2–25 | 3–15 |

*SS = Stainless Steel

The general procedure for preparation of the catalyst systems, after calcining the support, of the invention involves heating the alkali metal carbonate support to a temperature in the range of about 80° to about 350° C., preferably slightly above the melting point of the particular alkali metal used, cooling the particulate support and then contacting the particulate support with at least one elemental alkali metal in a dry, oxygen-free atmosphere, such as, for example $N_2$, Ar, or the like, at a temperature sufficient to cause the alkali metal to melt. The contacting, done in an oxygen-free atmosphere, is preferably carried out with suitable mixing to ensure even distribution. Suitable temperatures for the contacting step will vary with the particular alkali metal employed. For example, with elemental potassium, temperatures in the range of about 80° to 100° C. are preferred, while with elemental sodium, temperatures in the range of about 100° to 140° C. are preferred.

While the alkali metal treated support is maintained at or above the melting point of the particular alkali metal used, in an oxygen-free atmosphere, any desired promoter(s), such as for example, finely divided stainless steel or elemental copper, can be gradually added while the treated catalyst is continuously stirred. For example, with potassium, temperatures in the range of about 80° to about 100° C. are employed. The catalyst system is then ready to be charged to the reactor.

Optionally, the alkali metal carbonate support, once elemental alkali metal and any desired promoters have been deposited thereon, can be subjected to a subsequent heating step, in an oxygen-free atmosphere, to ensure as uniform a distribution as possible of the various promoters on the surface of the alkali metal carbonate support. Thus, the finished catalyst can be subjected to a temperature in the range of at least about 80° C. for a time in the range of about 0.1 to 4 hours. A temperature in the range of about 150° to about 250° C. for a time in the range of about 0.5–2 hours is presently preferred for the most uniform distribution.

Optionally, prior to charging the reactor, the catalyst system can be mixed with an inert substance to dilute the catalyst system and decrease the rate of olefin dimerization. Any inert substance which has no catalytic activity in an olefin dimerization reaction can be used. One example of such an inert substance is glass beads.

As indicated by the variety of supports, alkali metal components, and promoters included within the scope of the invention, numerous catalyst combinations are possible. Any combination of the alkali metal and optional promoters disclosed can be supported on any alkali metal carbonate support disclosed. Some possible combinations are described in detail in the examples which follow. The combination of support, alkali metal and promoter(s) which one may choose to employ will depend on a variety of variables such as for example, reactor configuration, reaction temperature and pressure, olefin feed employed, rate of olefin feed, and conversions desired.

Reactants

Reactants applicable for use in the process of the invention are olefinic compounds which can (a) self-react, i.e., dimerize, to give useful products such as, for example, the self-reaction of propylene gives 4-methyl-1-pentene; and/or (b) olefinic compounds which can react with other olefinic compounds, i.e., co-dimerize, to give useful products such as, for example, co-dimerization of ethylene plus propylene gives 1-pentene, co-dimerization of ethylene and 1-butene gives 3-methyl-1-pentene and so forth. As used herein, the term "dimerization" is intended to include both self-reaction and "co-dimerization" as defined above.

Suitable dimerizable olefinic compounds are those compounds having from about 3 to about 30 carbon atoms and having at least one olefinic double bond and at least one allylic hydrogen atom, i.e., at least one hydrogen atom attached to a carbon atom adjacent to a double-bonded carbon atom. Exemplary compounds include, but are not limited to, acyclic and cyclic olefins such as for example propylene, 1-butene, 2-butene, isobutylene, 1-pentene, 2-pentene, 1-hexene, 2-hexene, 3-hexene, 1-heptene, 2-heptene, 3-heptene, the four normal octenes, the four normal nonenes and so forth; 3-methyl-1-butene, 2-methyl-2-butene, 3-methyl-1-pentene, 3-methyl-2-pentene, 4-methyl-1-pentene, 4-methyl-2-pentene, tetramethylethylene and the like; cyclopentene, cyclohexene, methylcyclopentene, methylcyclohexene, and the like and mixtures of any two or more thereof.

Suitable co-dimerizable olefinic compounds are those compounds having from about 2 to about 30 carbon atoms, including all the compounds contemplated within the scope of "dimerizable" olefinic compounds as indicated above. In addition, olefinic compounds which do not have at least one allylic hydrogen atom are also included within the scope of co-dimerizable olefins. Exemplary compounds in addition to those indicated above, include, but are not limited to ethylene, 3,3-dimethyl-1-butene, ditertiarybutyl ethylene and the like and mixtures of any two or more thereof.

The compounds indicated above as dimerizable olefinic compounds are capable of undergoing both self-reaction, i.e., dimerization, and cross-reaction, i.e., co-dimerization, with other members of the same group or with those compounds designated as co-dimerizable. The co-dimerizable compounds which do not have at least one allylic hydrogen may be capable of isomerization to form an olefin having an allylic hydrogen under the reaction conditions employed. If such isomerization is not possible, then those non-isomerizable, co-dimerizable compounds which do not have at least one allylic hydrogen must be contacted with at least one of the "dimerizable" compounds in order to facilitate the desired co-dimerization reaction. In other words, the co-dimerizable compounds which do not have at least one allylic hydrogen atom and are not capable of isomerization to produce an olefin having at least one allylic hydrogen are therefore not capable of reacting with themselves under the reaction conditions employed for the dimerization reaction.

Reaction Conditions

The dimerization reaction of the invention can be carried out using either batch or continuous types of operation, although the catalysts of the invention are particularly well suited for continuous, fixed bed, operation. Suitable equipment such as for example autoclaves, tubular reactors and the like as are well known in the art can be employed. No special materials of construction are required so that steel, stainless steel, glass-lined reactors, or the like can be employed.

The reaction temperature can vary depending on the catalyst and feed(s) employed. Typically, a temperature range of about 50° to about 250° C. is suitable. Temperatures of about 80° to about 200° C. are preferred with a range of about 120° to about 170° C. most preferred because optimum reaction rates are obtained with minimum by-product formation.

The dimerization reaction can be carried out by contacting the dimerizable olefins with catalyst in the liquid phase or the gas phase, depending on the structure and molecular weight of the olefin, as well as reaction temperature and pressure employed. Pressure during the dimerization reaction can vary between wide limits. In general, higher pressures favor the progress of the reaction. Thus, pressures of atmospheric up to about 10,000 psig and higher are suitable. Preferably, pressures of about 100 to about 5,000 psig are employed, with pressure of about 1,000 to about 4,000 psig most preferred in order to achieve a good balance between reaction rate and minimize equipment and operating costs necessitated by very high reaction pressures.

If the reaction is carried out in the liquid phase, solvents or diluents for the reactants can be used. Saturated aliphatic hydrocarbons, e.g., pentane, hexane, cyclohexane, dodecane; aromatic compounds, preferably those without an alpha-hydrogen (which would be capable of undergoing alkylation under the reaction conditions) such as benzene and chlorobenzene are suitable. If the reaction is carried out in the gaseous phase, diluents such as aliphatic hydrocarbons, for example methane, ethane and/or substantially inert gases, e.g., nitrogen, argon, can be present.

The contact time required for the dimerization reaction depends upon several factors such as for example the activity of the catalyst, temperature, pressure, structure of the reactants employed, level of conversion desired, and the like. The length of time during which the dimerizable olefinic compounds are contacted with catalyst can vary conveniently between about 0.1 seconds and about 24 hours although shorter and longer contact times can be employed. Preferably, times of about one minute to about 5 hours are employed. Where reaction is carried out in continuous fashion, it is convenient to express the reactant/catalyst contact time in terms of weight hourly space velocity (WHSV), i.e., the ratio of the weight of reactant which comes in contact with a given weight of catalyst per unit time. Thus, a WHSV of about 0.1 to about 10 will be employed. A WHSV of about 0.5 to about 5 is preferred, with about 1 to about 4 WHSV most preferred for optimum catalyst productivity.

Products

The olefinic products of the invention have established utility in a wide variety of applications such as for example as monomers for use in the preparation of homopolymers, copolymers, terpolymers, e.g., as the third component of ethylene-propylene terpolymers useful as synthetic elastomers, and the like.

A further understanding of the present invention and its advantages will be provided by reference to the following examples.

EXAMPLES

In each of the following examples, typically, the dimerization of propylene was carried out in a steam heated 316 stainless steel tubular reactor ($\frac{1}{2}"\times 20"$). The catalyst system (27 grams; density about 0.84 g/mL), bounded above and below by small volumes of glass beads, was combined with 25 grams of an inert substance, i.e., no dimerization catalytic activity, to dilute the catalyst system and thus reduce and control the reaction rate. The contents of the tubular reactor were heated to the reaction temperature of about 160° C. at about 1500 psig and propylene was pumped into the reactor at a rate of about 120 mL/hr. After about 1.5 hours of reaction time and each one hour thereafter for the following 6 hours, a sample was collected and analyzed by gas liquid chromatography (glc). The summarized results represent the analysis of the last dimerization sample collected.

Example 1

(Granular Support)

Granular catalyst support was prepared from commercially available, anhydrous potassium carbonate (J. T. Baker or Diamond Shamrock, ACS reagent grade), acetone (ACS reagent grade), and deionized water. Water and acetone were pre-mixed and added to potassium carbonate, particle size of equal to or less than about 0.42 mm (40 mesh), to form a thick paste. Usually, about 2 milliliters of liquid were added to about 1 gram of potassium carbonate. The thick paste was thoroughly mixed and then dried at about 85° C. in a vacuum oven for at least 2 hours in the presence of air. The dried paste was ground to about 6 mesh and calcined at about 250° C. for about 3 hours in an oxygen-containing atmosphere.

The resultant support was allowed to cool, in an oxygen-free atmosphere, to about 80° to about 85° C., at which time about 5 weight percent of elemental potassium and about 5 weight percent of finely divided 316 stainless steel (about 325 mesh) were added. The catalyst support and catalyst system were kept under dry, inert atmosphere.

Catalysts and the results of the corresponding propylene dimerization reactions are summarized in Table I.

TABLE I

| Run No. | Solvent System, Vol. % | Crush Strength, pounds (avg.) | Propylene Conv., % | Selectivity to 4MP1, % | 4MP1/4MP2 |
|---|---|---|---|---|---|
| 101 | 100 H$_2$O | 3.00 | 21.9 | 88.0 | 19 |
| 102 | 100 H$_2$O | — | 17.4 | 85.7 | 13 |
| 103 | 75 H$_2$O/ 25 acetone | 3.72 | 24.7 | 88.9 | 26 |
| 104 | 75 H$_2$O/ 25 acetone | 4.40 | 25.6 | 87.5 | 18 |
| 105 | 50 H$_2$O/ 50 acetone | — | 15.8 | 88.4 | 24 |

The catalyst supports in Runs 101, 103, and 105 were prepared using J. T. Baker potassium carbonate. The catalyst supports in Runs 102 and 104 were prepared using Diamond Shamrock potassium carbonate.

After the propylene dimerization, each catalyst system was removed from the dimerization reactor and examined. Each catalyst system in Table I showed some fines, but little damage.

Comparison of the percent propylene conversion, percent selectivity to 4-methylpentene-1 (4MP1), and the 4MP1/4MP2 ratio indicate that catalysts made with catalyst supports prepared using water and acetone produce better results than catalysts made with catalyst supports prepared with only water.

The examples have been provided merely to illustrate the practice of the invention and should not be read so as to limit the scope of the invention or the appended claims in any way. Reasonable variations and modifications, not departing from the essence and spirit of the invention, are contemplated to be within the scope of patent protection desired and sought.

That which is claimed is:

1. A process for the preparation of a catalyst support comprising:
   (a) preparing a thick paste comprising about 65 to about 75 weight percent of an alkali metal carbonate, about 11 to about 19 weight percent of water, and about 9 to about 19 weight percent of a water soluble ketone;
   (b) forming a particulate product from said paste; and
   (c) calcining said particulate product.

2. A process for producing a catalyst which comprises contacting the support prepared in accordance with claim 1 with at least one elemental alkali metal in an oxygen-free atmosphere at a temperature sufficient to cause the alkali metal to melt.

3. A process according to claim 2 further comprising contacting said catalyst with at least one promoter selected from the group consisting of finely divided stainless steel, elemental copper, elemental cobalt, finely divided glass, and mixtures thereof.

4. A process according to claim 2 wherein said elemental alkali metal is potassium.

5. A process according to claim 2 wherein said elemental alkali metal is about 1 to about 20 weight percent of said catalyst.

6. A process according to claim 1 wherein said alkali metal carbonate is selected from the group consisting of sodium carbonate and potassium carbonate.

7. A process in accordance with claim 1 wherein said particulate product is formed by:
   (a) drying said thick paste under conditions suitable to remove essentially all water and water soluble ketone from said paste;

(b) crushing the dried product of step (a); and
(c) collecting a uniform particle size particulate product.

8. A process in accordance with claim 1 wherein said particulate product is formed by:
   (a) extruding said thick paste to form an extrudate; and
   (b) drying said extrudate of step (a) under conditions suitable to remove essentially all water and water soluble ketone from said extrudate.

9. A process in accordance with claim 1 wherein said thick paste further comprises a carbonaceous compound selected from the group consisting of carbon black, charcoal, coconut charcoal, amorphous graphite, crystallite graphite, and mixtures thereof.

10. A process according to claim 9 wherein said carbonaceous compound is about 0.01 to about 5 weight percent of said support.

11. A process in accordance with claim 1 wherein said water soluble ketone is an aliphatic ketone containing from about 3 to about 7 carbon atoms.

12. A process according to claim 1 wherein said aliphatic ketone is selected from the group consisting of 2-propanone, 2-butanone, 2-pentanone, 2-hexanone, and mixtures thereof.

13. The catalyst produced by the process of claim 2.

14. The catalyst produced by the process of claim 3.

15. A process according to claim 1 wherein said particulate product is calcined in an oxygen containing atmosphere at a temperature in the range of about 80° C. to about 350° C.

16. A process for the preparation of a catalyst support comprising:
   (a) preparing a thick paste comprising potassium carbonate, water, and acetone;
   (b) forming a particulate product from said paste; and
   (c) calcining said particulate product.

17. A process for producing a catalyst which comprises contacting the support prepared in accordance with claim 1 with elemental potassium in an oxygen-free atmosphere at a temperature sufficient to cause the elemental potassium to melt.

* * * * *

UNITED STATES PATENT AND TRADEMARK OFFICE
CERTIFICATE OF CORRECTION

PATENT NO. :     4,895,819

DATED       :    January 23, 1990

INVENTOR(S) :    Charles A. Drake

It is certified that error appears in the above-identified patent and that said Letters Patent is hereby corrected as shown below:

Claim 12, line 1, delete "1" and substitute --- 11 --- therefor.

Signed and Sealed this

Twenty-first Day of April, 1992

Attest:

HARRY F. MANBECK, JR.

Attesting Officer

Commissioner of Patents and Trademarks